United States Patent
Katsushima

(10) Patent No.: US 10,498,974 B2
(45) Date of Patent: Dec. 3, 2019

(54) RADIATION IMAGE CAPTURING APPARATUS AND RADIATION IMAGE CAPTURING SYSTEM

(71) Applicant: KONICA MINOLTA, INC., Chiyoda-ku, Tokyo (JP)

(72) Inventor: Kazuhiko Katsushima, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 16/029,864

(22) Filed: Jul. 9, 2018

(65) Prior Publication Data
US 2019/0028657 A1 Jan. 24, 2019

(30) Foreign Application Priority Data

Jul. 19, 2017 (JP) .................. 2017-139604

(51) Int. Cl.
| | | |
|---|---|---|
| H04N 5/30 | (2006.01) | |
| G01T 1/20 | (2006.01) | |
| G16H 30/40 | (2018.01) | |
| A61B 6/00 | (2006.01) | |
| H04M 1/725 | (2006.01) | |
| G06F 17/22 | (2006.01) | |

(52) U.S. Cl.
CPC .............. *H04N 5/30* (2013.01); *A61B 6/4266* (2013.01); *A61B 6/4405* (2013.01); *A61B 6/461* (2013.01); *A61B 6/467* (2013.01); *A61B 6/54* (2013.01); *A61B 6/566* (2013.01); *G01T 1/20* (2013.01); *G16H 30/40* (2018.01); *H04M 1/72561* (2013.01); *A61B 6/5205* (2013.01); *G06F 17/2247* (2013.01)

(58) Field of Classification Search
None
See application file for complete search history.

(56) References Cited

U.S. PATENT DOCUMENTS

| | | | |
|---|---|---|---|
| 8,107,590 B2 | 1/2012 | Nishino et al. | |
| 2013/0038738 A1* | 2/2013 | Ando | A61B 6/4266 348/162 |
| 2013/0080583 A1* | 3/2013 | Takagi | G06F 21/84 709/217 |
| 2017/0153333 A1* | 6/2017 | Morita | G01T 1/17 |

FOREIGN PATENT DOCUMENTS

JP 2010051523 A 3/2010

\* cited by examiner

*Primary Examiner* — Eileen M Adams
(74) *Attorney, Agent, or Firm* — Holtz, Holtz & Volek PC

(57) ABSTRACT

A radiation image capturing apparatus includes the following. A radiation detector includes a substrate in which a plurality of radiation detecting elements are arranged two-dimensionally. The plurality of radiation detecting elements receive radiation and generate charge in an amount according to an amount of received radiation. A reader reads the amount of charge generated in each of the plurality of radiation detecting elements as a signal value, and generates image data based on the signal value. A storage stores the image data generated by the reader. A hardware processor transmits the image data stored in the storage to an external terminal and an external device.

5 Claims, 4 Drawing Sheets

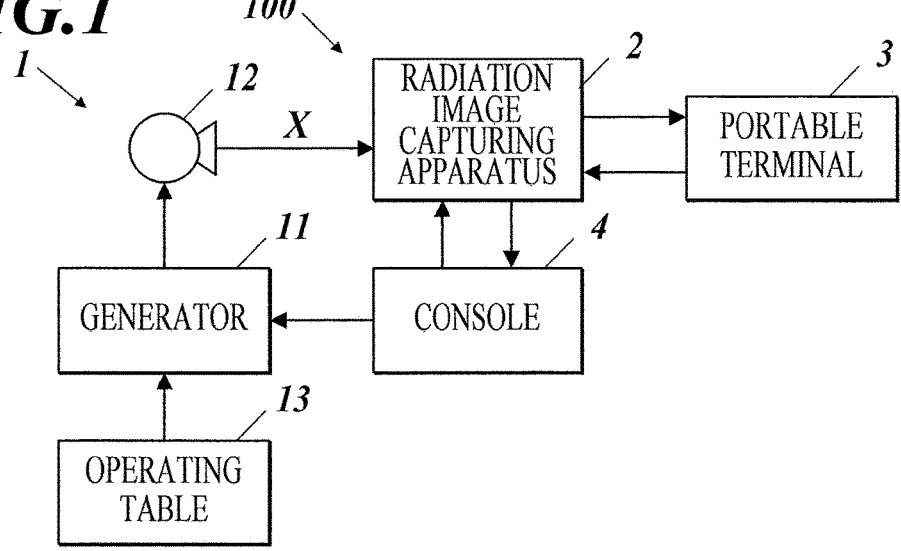
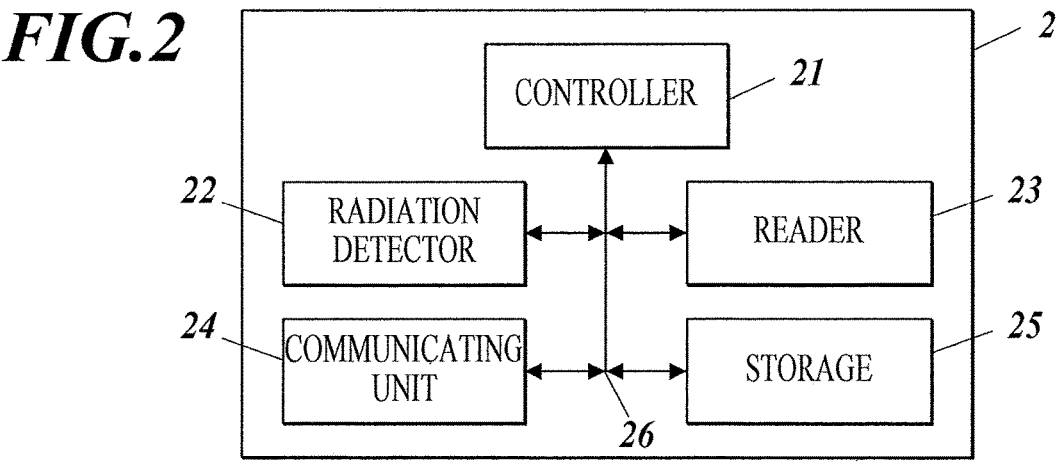
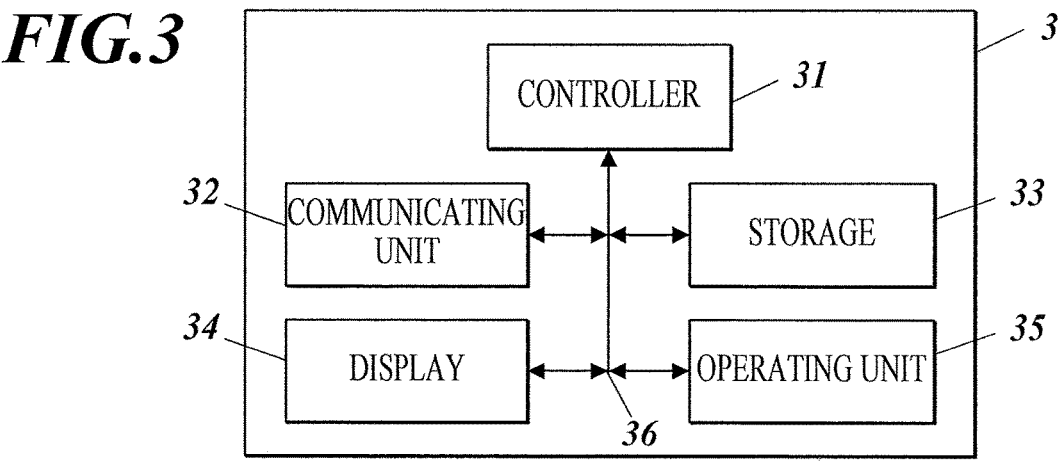

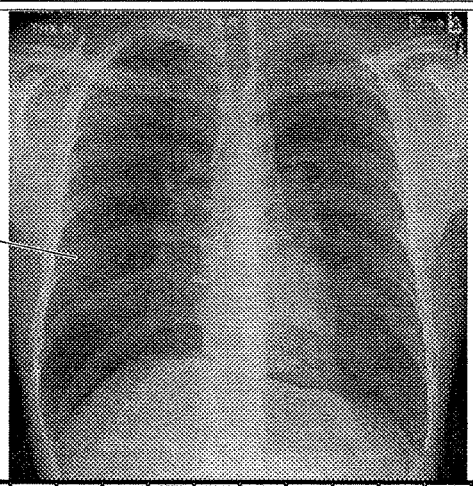

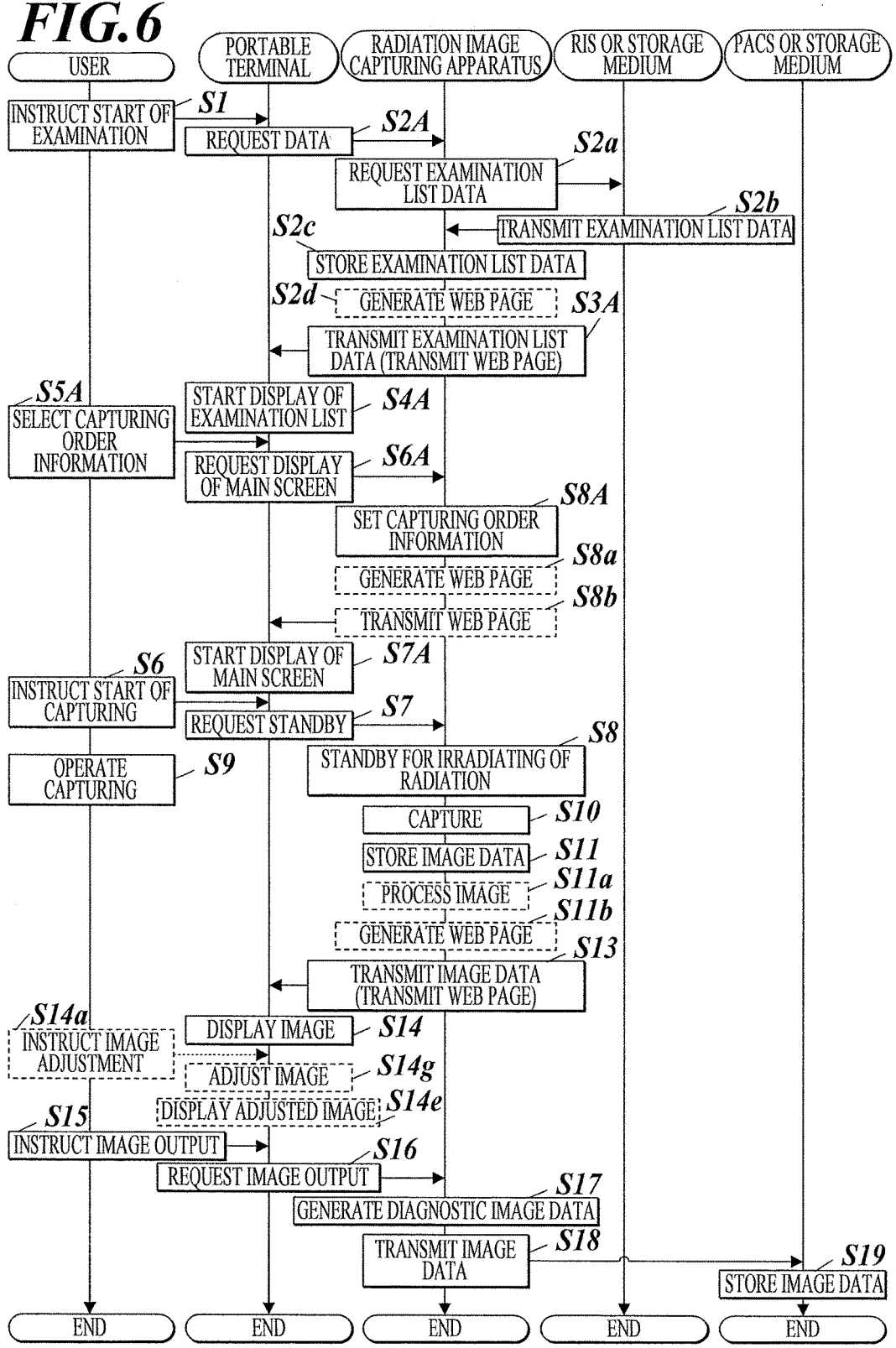

RADIATION IMAGE CAPTURING APPARATUS AND RADIATION IMAGE CAPTURING SYSTEM

BACKGROUND

1. Technological Field

The present invention relates to a radiation image capturing apparatus and a radiation image capturing system including such apparatus.

2. Description of the Related Art

Lately, portable radiation image capturing systems are being developed. Typically, such portable radiation image capturing system includes a panel-type radiation image capturing apparatus (also called a FPD (Flat Panel Detector)) and an examination car provided with a radiation irradiating apparatus. By using such system, a user (radiation technician) is able to go to a capturing location with the system and perform a series of operations such as capturing and image confirmation at the location. Therefore, it is possible to easily capture radiation images of patients who have difficulty in moving.

Specifically, for example, there is a technique which is provided with a panel-type radiation image capturing apparatus including a display, and the capturing conditions and the captured images are displayed on the display (Japanese Patent Application Laid-Open Publication No. 2010-051523).

The radiation image capturing system described in Japanese Patent Application Laid-Open Publication No. 2010-051523 needs a console to perform management of various pieces of information, processing of image data, and output of image data to external systems. Therefore, such radiation image capturing systems become highly expensive, and this made it difficult to be employed in small hospitals.

Also, the radiation image capturing apparatus according to Japanese Patent Application Laid-Open Publication No. 2010-051523 is formed as one with the display. Therefore, it may be difficult to confirm the display depending on how the capturing is performed (for example, when the radiation image capturing apparatus is used inserted between a bed and a laid patient).

SUMMARY

The present invention is conceived in view of the above problems, and an object of the present invention is to provide a radiation image capturing system which is low in cost and in which capturing conditions and capturing images can be confirmed easily.

To achieve at least one of the abovementioned objects, according to an aspect of the present invention, a radiation image capturing apparatus reflecting one aspect of the present invention is described, the apparatus including, a radiation detector which includes a substrate in which a plurality of radiation detecting elements are arranged two-dimensionally, the plurality of radiation detecting elements receiving radiation and generating charge in an amount according to an amount of received radiation; a reader which reads the amount of charge generated in each of the plurality of radiation detecting elements as a signal value, and generates image data based on the signal value; a storage which stores the image data generated by the reader; and a hardware processor which transmits the image data stored in the storage to an external terminal and an external device.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

FIG. 1 is a schematic diagram showing a radiation image capturing system according to the present invention.

FIG. 2 is a block diagram showing a configuration of a radiation image capturing apparatus included in the radiation image capturing system shown in FIG. 1.

FIG. 3 is a block diagram showing a configuration of a portable terminal included in the radiation image capturing system shown in FIG. 1.

FIG. 4A is an example of a list screen displayed on a display included in the portable terminal shown in FIG. 3.

FIG. 4B is an example of a main screen displayed on a display included in the portable terminal shown in FIG. 3.

FIG. 6 is a ladder chart showing an operation of a radiation image capturing system regarding a modification.

DETAILED DESCRIPTION OF EMBODIMENTS

Figure 5:
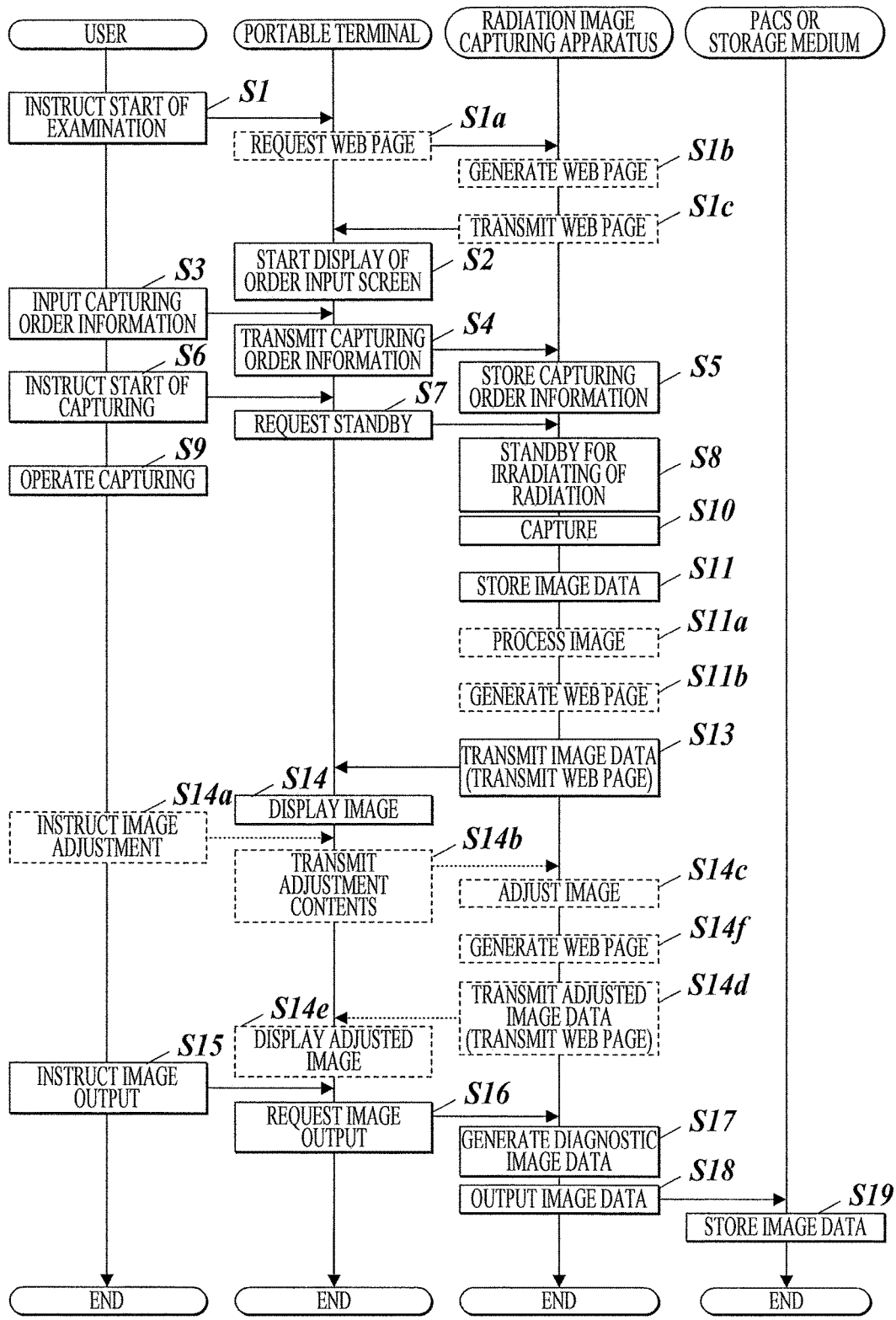
FIG. 5 is a ladder chart showing an operation of the radiation image capturing system shown in FIG. 1.

Hereinafter, one or more embodiments of the present invention will be described in detail with reference to the drawings. However, the scope of the invention is not limited to the illustrated examples.

[Configuration of Radiation Image Capturing System]

First, a configuration of a radiation image capturing system 100 according to the present invention is described. FIG. 1 is a schematic configuration diagram of the radiation image capturing system 100 according to the present invention.

As shown in FIG. 1, the radiation image capturing system 100 according to the present invention includes a radiation irradiating apparatus 1, a radiation image capturing apparatus 2, and a portable terminal 3.

The radiation image capturing system 100 does not need a console, and is able to directly communicate with a Radiology Information System (RIS), a Picture Archiving and Communication System (PACS), and the like.

The radiation irradiating apparatus 1 includes a generator 11, a radiation source 12, and an operating table 13.

The generator 11 applies to the radiation source 12 voltage according to the tubular voltage, tubular current, irradiating time (mAs value), etc. set by the console 4.

The radiation source 12 includes a rotating anode (not shown) which is able to generate radiation or a filament which irradiates an electron beam on the rotating anode. The radiation source 12 generates the radiation X in the amount according to the voltage applied from the generator 11.

The operating table 13 includes an operating unit and an emitting switch which can be operated by the user (radiation technician, etc.). Then, the various capturing conditions (conditions regarding the irradiating of radiation such as tubular voltage, tubular current, irradiating time, current time product) can be set by operating the operating table 13. The start of irradiation of radiation (applying voltage) can be instructed to the generator 11 by operating the emitting switch on the operating table 13.

The radiation irradiating apparatus 1 may be moved when provided on a diagnosis car.

The radiation image capturing apparatus 2 reads the image data when irradiation of radiation is received from the radiation irradiating apparatus 1. Then, the radiation image capturing apparatus 2 holds the read image data or transmits the image data to the portable terminal 3.

The radiation image capturing apparatus 2 may be a dedicated type formed as one with a capturing stage or a portable type (cassette). Preferably, a portable type is employed so that the radiation irradiating apparatus 1 can be moved.

The details of the radiation image capturing apparatus 2 will be described later.

The portable terminal 3 confirms the radiation image captured in the radiation image capturing apparatus 2. The configuration of the portable terminal 3 is not limited, but is preferably a commercially available portable terminal such as a smartphone or tablet which can be transported.

The portable terminal 3 can be connected to be able to communicate with one or a plurality of radiation image capturing apparatuses 2, and is able to display the display image based on the image data received from the radiation image capturing apparatus 3.

The details of the portable terminal 3 will be described later.

[Configuration of Radiation Image Capturing Apparatus]

Next, the details of the radiation image capturing apparatus 2 included in the radiation image capturing system 100 is described. FIG. 2 is a block diagram showing the radiation image capturing apparatus 2.

As shown in FIG. 2, the radiation image capturing apparatus 2 includes a controller 21, a radiation detector 22, a reader 23, a communicating unit 24, a storage 25, and the like The units 21 to 25 are connected to each other through a bus 26. Power is supplied to each unit 21 to 25 from the internal power.

The controller 21 collectively controls the operation of each unit in radiation image capturing apparatus 2 with a CPU, a RAM, etc. Specifically, when the power switch is turned on, a predetermined control signal is received from the radiation irradiating apparatus 1, or the radiation is received from the radiation irradiating apparatus 1, the controller 21 reads various processing programs stored in the storage 25, deploys the program in the RAM, and executes the various processes according to the processing programs.

The radiation detector 22 includes a substrate in which a plurality of radiation detecting elements which generates charge in an amount according to the amount of received radiation are arranged two-dimensionally and a conventionally well-known device can be used.

That is, the radiation image capturing apparatus 2 includes a scintillator. The radiation image capturing apparatus 2 can be an indirect type in which the emitted light is detected when the scintillator receives the radiation or a direct type in which the radiation is directly detected without the scintillator.

The radiation image capturing apparatus 2 may be a linked type in which the accumulation of charge is started on the basis of the signal from the radiation irradiating apparatus 1 or a non-linked type in which the accumulation of charge is started without the signal from the radiation irradiating apparatus 1 when the radiation image capturing apparatus 2 detects the irradiation of radiation.

The reader 23 reads the amount of charge generated in the plurality of radiation detecting elements as the signal value. The reader 23 which is configured to be able to generate the image data based on the signal values can be used and a conventionally well-known device can be used.

The communicating unit 24 includes a network interface. The communicating unit 24 is connected to a portable terminal 3 or an external system such as RIS or PACS through a communication network such as a LAN (Local Area Network), a WAN (Wide Area Network), the Internet, etc. The communicating unit 24 transmits and receives data between the above.

The communicating unit 24 may be provided with a communication interface such as a NFC, and use, for example, short range wireless communication so that data can be transmitted and received in an environment cut off from a communication network. Alternatively, the communicating unit 24 may be connected to an external system by wired communication.

The radiation image capturing apparatus may be provided with a media slot or port (not shown) other than the communicating unit 24, and the data can be input and output between various storage media such as a USB memory. Hereinafter, when the external system and the storage medium are not distinguished, these may be collectively called external devices.

The storage 25 includes a HDD (Hard Disk Drive), a semiconductor memory, and the like. The storage stores various processing programs (various image processing programs, web server programs, etc.) and parameters or files necessary to execute the programs.

The storage 25 is able to store image data generated by the reader 23 and is able to store capturing order information (patient information, capturing site, capturing direction, and various capturing conditions of the capturing target) linked to image data.

Comments at the time of capturing can be stored linked with the image data.

The controller 21 of the radiation image capturing apparatus 2 operates as described below according to a process program stored in the storage 25.

For example, the controller 21 is able to receive capturing order information from the portable terminal 3 or the external apparatus or to receive adjustment contents for image data from the portable terminal 3 by using the communicating unit 24.

The controller 21 is able to transmit generated image data to the portable terminal 3 and the external device by using the communicating unit 24. The output of the image data can be performed automatically when the image data is generated. Alternatively, the image data may be output when connected to the network, when communication is possible with the portable terminal 3 or the external devices, or when a request for transmission is received from the portable terminal 3 or the external devices. The image data can be divided and output a plurality of times.

The controller 21 is able to transmit information such as the following to the portable terminal 3 by using the communicating unit 24, remaining battery charge for the radiation image capturing apparatus 2, the radio wave strength of the wireless communication, identification information such as name or serial number, capturing status (information showing whether radiation can be detected such as, in preparation, capturing possible, in process), stored number of captured images, remaining free space to store data.

The controller 21 and the communicating unit 24 function as the communicating means of the present invention by performing the above operations.

Instead of using the communicating unit 24, the information can be output using a storage medium. In this case, the controller 21 or the media slot functions as the communicating means of the present invention.

The controller 21 may have the function to obtain one or a plurality of pieces of past image data from the external device using the communicating unit 24. The past image data includes capturing conditions (kV, mAs, SID, existence of grid) and image processing parameters.

The controller 21 is able to perform a predetermined image process on Raw image data generated by the reader 23 and generated at least one type of processed image data automatically or in reply to a request from the portable terminal 3. That is, the controller 21 functions as the image generating means according to the present invention.

The image process performed here can be largely divided between a correction process and an image process for display. Examples of the correction process include, an offset correction, gain correction, defect correction, scattered radiation removal process and the like. Examples of the image process for display include noise reduction process, frequency process, gradation process, space conversion (rotation/inversion), and the like. According to the above processes, various types of images for display can be generated (preview image data applying a simple process, and diagnostic image data applying a full process).

Such image correction functions can be included in a portable terminal 3 or an external system instead of the radiation image capturing apparatus 2.

The image processing function may be included in at least two among the radiation image capturing apparatus 2, the portable terminal 3, and the external system, and the apparatus which performs the image process can be determined based on the processing abilities and the communication speed of each apparatus.

Further, the image processing function may be included in at least two among the radiation image capturing apparatus 2, the portable terminal 3, and the external system, and when the plurality of image processes can be performed in any order, the image processes can be performed parallel in the devices.

When the controller 21 stores the processed image data, the parameters applied in the process for the processed image data can be included. With this, when the image process needs to be performed again on the same image data, the process can be performed promptly.

As for the processed image data with a low process cost, only the parameters used in the process may be stored instead of storing the image data in the storage 25. This is because compared to data with a high process cost, there is not much burden even if the image process is performed each time. With this, the capacity of the storage 25 of the radiation image capturing apparatus 2 can be saved.

[Configuration of Potable Terminal]

Next, the details of the portable terminal 3 included in the radiation image capturing system 100 are described. FIG. 3 is a block diagram showing a configuration of a portable terminal 3. FIG. 4A and FIG. 4B are examples of a screen displayed on the portable terminal.

As shown in FIG. 3, the portable terminal 3 includes a controller 31, a communicating unit 32, a storage 33, a display 34, and an operating unit 35. The units 31 to 35 are connected to each other through a bus 36. An internal power supply (not shown) supplies electric power to the units 31 to 35.

The controller 31 centrally controls the operation of each unit included in the portable terminal 3 with the CPU, the RAM, etc. Specifically, in response to receiving the operation signal from the operating unit 35 or receiving various signals and data from the radiation image capturing apparatus 2, various processing programs stored in the storage 33 are read and deployed in the RAM, various processes are performed according to the process program, and the contents displayed on the display 34 are controlled.

The communicating unit 32 includes a network interface, and transmits and receives data with an external system connected through a communication network such as a LAN (Local Area Network), WAN (Wide Area Network), the Internet, and the like.

The communicating unit 32 may be provided with a communication interface such as a NFC, and use, for example, short range wireless communication so that data can be transmitted and received in an environment cut off from a communication network. Alternatively, the communicating unit 24 may be connected to an external system by wired communication.

The storage 33 includes a HDD (Hard Disk Drive) and a semiconductor memory, and stores various processing programs (system program, and application programs such as a web browser) and parameters and data necessary to execute the programs.

The display 34 includes a monitor such as a LCD, etc., and displays various screens according to an instruction of a display signal received from the controller 31.

The operating unit 35 includes a keyboard provided with various keys, a pointing device such as a mouse, or a touch panel layered on the display 34. The operating unit 35 outputs to the controller 31 the operating signal input according to the operation of the keys on the keyboard, operation of the mouse, or the position touched on the touch panel.

The controller 31 of the portable terminal 3 performs the following operations according to the processing program stored in the storage 33.

For example, the controller 31 controls the display 34 to display the list screen L of the capturing order information as shown in FIG. 4A, or the main screen M including the display region R of the image I for display in the center as shown in FIG. 4B.

The controller 31 receives the operation (input operation or selection operation) operated on the operating unit 35. The contents (capturing order information input or selected or instruction to adjust image data) can be transmitted to the radiation image capturing apparatus 2.

The list screen L, the main screen M, and the display image I displayed on the screen can be displayed using the console application installed in the portable terminal 3 in a separate occasion. Preferably, the above are displayed as web contents displayed on a browser originally included in the portable terminal 3. When the browser is used, the data of the processing target and the processing program are transmitted in a series of capturing operations. Therefore, applications do not have to be explicitly installed in the portable terminal 3. As a result, compared to when all console applications are transmitted for a specific processing program, the transmitting time of the processing program can be shortened. Moreover, even if there is trouble in the portable terminal 3 or the portable terminal 3 runs out of batteries, other typical portable terminals can be used instead. Further, maintenance such as update of application in the portable terminal 3 due to update of programs in the console 4 or the radiation image capturing apparatus 2 is not necessary.

The process program may also be web contents and can be transmitted to the portable terminal 3. In this case, preferably, the format is to be Java Script (registered trademark) or Web Assembly which can be executed on a web browser.

The voice data, the icon image, and the animation data executed on the portable terminal 3 may also be web contents.

When the image I for display is displayed on the browser, the radiation image capturing apparatus 2 needs to function as a web server. Therefore, the storage 25 of the radiation image capturing apparatus 2 stores the web server program and the web application program.

When the display image I is displayed on the browser, the radiation image capturing apparatus 2 generates web contents of the image I for display from the image data in response to a request from the portable terminal 3, and the radiation image capturing apparatus 2 transmits the web contents to the portable terminal 3. In this case, the controller 21 functions as the contents generating unit according to the present invention.

When the radiation image capturing apparatus 2 has a function to store the parameters applied in the process, the visibility of the overlay display can be changed depending on whether the parameters from the past image are automatically transferred or adjusted manually.

When the image is adjusted, the present value of the parameter for adjustment can be displayed.

When the radiation image capturing apparatus 2 includes the function to obtain the past image data from the external device, the past image based on the past image data may be displayed on the display 34. In such case, the plurality of past images may be displayed as a list on the display 34 and the screen may be switched.

The capturing conditions and the processing parameters used in the past may be displayed together with the past image (overlay, etc.). With this, the user can refer to the capturing performed in the past.

When the processing program which can be executed on the web browser is included in the web contents, the process to perform the image correction (gain correction, offset correction or the defect correction) on the image data received from the radiation image capturing apparatus 2 may be included as the processing program. According to the above, the differences in the image data caused by the different radiation image capturing apparatuses 2 can be corrected.

The processing program may include processes to cache the obtained processing program in the web browser or obtain the processing program again only if the version is different. According to the above, the processing program does not have to be received when the same image processes are performed. This is preferable from the viewpoint of accelerating display.

The processing program may omit some of the image processes to be executed or include a process to return the data so that some of the processes are executed in the radiation image capturing apparatus 2 depending on the importance of the process or the cost of the process. This prevents a heavy burden on the controller 31 of the portable terminal 3.

The processing program may include a process to erase the image data or the parameters stored in the storage 33 in response to the operation to end the web browser or to end capturing. According to the above, the individual information of the patient does not remain in the portable terminal 3 after the capturing ends. This is preferable from the viewpoint of security.

When the order information is input, the controller 31 can include the function to generate master information combining the capturing site, the capturing direction, various capturing conditions and the image processing parameters, and to store the information in the storage 35.

The master information may be obtained from the external devices instead of generating in the portable terminal 3.

The master information may be generated in the controller 21 of the radiation image capturing apparatus 2 and stored in the storage 25.

[Operation of Radiation Image Capturing System]

Next, the operation of the radiation image capturing system 100 is described. FIG. 5 is a ladder chart showing the flow from the radiation image capturing to display using the radiation image capturing system 100 according to the present embodiment.

As shown in FIG. 5, first, when the user instructs the start of the examination (step S1), the input screen for the capturing order information is displayed on the portable terminal 3 (step S2).

When the input screen is displayed on the browser, after step S1, the portable terminal 3 transmits to the radiation image capturing apparatus 2 the signal to request the web contents for the input screen (step S1a). Then, the radiation image capturing apparatus 2 creates the web contents for the input screen (step S1b), and transmits the data to the portable terminal 3 (step S1c). With this, the display of the input screen starts.

Then, when the user inputs the capturing order information on the input screen (step S3), the portable terminal 3 transmits the input capturing order information to the radiation image capturing apparatus (step S4).

Then, when the radiation image capturing apparatus 2 receives the capturing order information, the capturing order information is stored (step S5).

When the master information combining the capturing site, the capturing direction, various capturing conditions, the image processing parameters, etc. are employed as described above, the master information is generated and stored or obtained from external devices, before or after step S4 or in parallel with step S4.

When the master information is held in the radiation image capturing apparatus 2, the data is exchanged between the portable terminal 3 and the radiation image capturing apparatus 2 each tune the capturing menu is selected in the portable terminal 3, and a portion of the screen is updated or the screen is switched. If the portable terminal 3 holds the above-described master information, a main screen M can be made and the input on the portable terminal 3 can be simplified.

Then, when the user instructs the start of capturing (step S6), the portable terminal 3 transmits the signal to request standby to the radiation image capturing apparatus 2 (step S7).

Then, when the radiation image capturing apparatus 2 receives a signal requesting standby, the radiation image capturing apparatus 2 stands by in a state ready for capturing (step S8).

While the radiation image capturing apparatus 2 is standing by, when the user confirms the name of the patient and the capturing order information displayed on the input screen, and the capturing operation, that is, the emitting switch is pressed (step S9), the radiation irradiating apparatus 1 irradiates radiation to the patient (radiation image capturing apparatus 2), the radiation image capturing apparatus 2 performs capturing (generates image data) (step S10), and the image data is stored in the storage 33 (step S11). Then, the image data is transmitted to the portable terminal 3 (step S13).

Then, when the portable terminal 3 receives the image data, the display image I is displayed based on the data (step S14).

When the radiation image capturing apparatus 2 includes the image processing function, the radiation image capturing apparatus 2 performs the image process before or after step S11 or in parallel with step S11 (step S11a).

When the display image I is displayed on the browser, the web contents of the display image I is generated after step S11 or step S11a (step S11b), and the data is transmitted to the portable terminal 3 in step S13. With this, the display of the display image I is started.

After step S14, the user confirms the capturing image displayed on the portable terminal 3, and when the user determines that there is a problem in the results of the capturing, the user instructs adjustment of the image (step S14a). Then, the portable terminal 3 transmits the adjustment contents of the image to the radiation image capturing apparatus 2 (step S14b).

Then, when the radiation image capturing apparatus 2 receives the adjustment contents, the radiation image capturing apparatus 2 adds the adjustment to the image data to generate the adjusted image data (step S14c), and the adjusted image data is transmitted to the portable terminal 3 (step S14d).

Then, when the portable terminal 3 receives the adjusted image data, the adjusted image is displayed on the basis of the adjusted image data (step S14e).

When the adjusted image is displayed on a browser, after step S14c, the web contents of the adjusted image is generated (step S14f), and the data is transmitted to the portable terminal 3 in step S14d. With this, the adjusted image is displayed.

Here, when only the image is changed as in the image adjustment, only the image data may be transmitted instead of the entire web contents.

The adjustment of the image data may be performed on the portable terminal 3.

After step S14 or step S14e, when the user confirms the captured image displayed on the portable terminal 3, determines that there is no problem with the captured result, and instructs the output of the image data (step S15), the portable terminal 3 transmits a signal to request output of image data to the radiation image capturing apparatus 2 (step S16).

Then, when the radiation image capturing apparatus 2 receives a signal to request output of image data, the radiation image capturing apparatus 2 adds the necessary image process to the image data and generates the diagnostic image data (step S17).

When the various images are displayed with the application, after step S16, the stored image data is erased as necessary.

After capturing, when the user connects the radiation image capturing apparatus 2 to the external device, the radiation image capturing apparatus 2 outputs the stored various image data to the external device (step S18). Then, the external device stores the image data (step S19). Then, the series of capturing ends.

(Modification)

The radiation image capturing system according to the present embodiment can be configured so that the capturing order information is input from the external device instead of the portable terminal 3, or the image data is adjusted in the portable terminal 3.

Specifically, the storage 25 of the radiation image capturing apparatus 2 is provided with a region to store the examination list included in the plurality of pieces of capturing order information. The storage 25 is provided with a function to obtain data of the examination list from the RIS or the storage medium based on the request for the web contents of the examination list from the portable terminal 3, and a function to generate the web contents based on the obtained examination list.

The web contents include the image process program which can be executed on the web browser.

Next, the operation of the radiation image capturing system 100 to obtain the order information from the external device and to output the order information of the external device is described. FIG. 6 is a ladder chart showing a flow from the radiation image capturing to the display using the radiation image capturing system 100 according to a modification of the embodiments.

As shown in FIG. 6, first, when the user instructs the start of the examination (step S1), the portable terminal 3 transmits to the radiation image capturing apparatus 2 the signal requesting data in order to display the examination list (step S2A).

Then, when the radiation image capturing apparatus 2 receives the signal, the radiation image capturing apparatus 2 transmits a signal to request the data of the examination list to the RIS (step S2a).

Then, when the RIS receives the signal, the data of the examination list is transmitted to the radiation image capturing apparatus 2 (step S2b).

In step S2b, the past data regarding the capturing order information included in the examination list may be obtained from PACS, etc.

Then, when the radiation image capturing apparatus 2 receives the data of the examination list, the data is stored (step S2c). Then, the data is transmitted to the portable terminal 3 (step S3A).

Then, when the portable terminal 3 receives the data of the examination list screen, the examination list is displayed based on the data (step S4A).

When the examination list is displayed with the browser, the web contents of the examination list is generated after step S2c (step S2d), and the data is transmitted to the portable terminal 3 in step S3A. With this, the display of the examination list starts.

Then, when the user selects the capturing order information from the examination list screen (step S5A), the portable terminal 3 transmits the selected capturing order information to the radiation image capturing apparatus 2 (step S6A), and the main screen corresponding to the selected capturing order information is displayed (step S7A).

After step S6A, the radiation image capturing apparatus 2 receives the signal, and sets the corresponding capturing order information (step S8A).

When the main screen is displayed on the browser, in step S6A, the portable terminal 3 transmits to the radiation image capturing apparatus 2 the signal to request the web contents of the main screen corresponding to the selected capturing order information. After step S8A, the radiation image capturing apparatus 2 generates the web contents of the examination list (step S8a), and the data is transmitted to the portable terminal 3 (step S8b). With this, the main screen is displayed.

The flow from the step S6 to step S14 is similar to the above embodiment.

After step S14, the user confirms the capturing image displayed on the portable terminal 3, when the user determines there is a problem with the capturing results, similar to the above embodiment, the user instructs the adjustment of the image (step S14a). According to the present modification, the image adjustment is performed in the portable terminal 3, the portable terminal 3 adds the adjustment to the image data and generates the adjusted image data (step S14g). Then, the adjusted image data is displayed (step S14e). The image adjustment can be performed with the flow similar to the above embodiment (see FIG. 5), and the radiation image capturing apparatus 2 can perform the image adjustment.

The flow after step S15 is similar to the above embodiment.

As described above, the radiation image capturing apparatus 2 of the radiation image capturing system 100 according to the present embodiment includes a radiation detector 22 which includes a substrate in which a plurality of radiation detecting elements are arranged two dimensionally, the radiation detecting elements which generate charge in an amount according to an amount of received radiation, a reader 23 which reads the amount of charge generated by each of the plurality of radiation detecting elements as a signal value and which generates image data based on the signal values, a storage 25 which stores image data generated by the reader 23, and a communicating unit which transmits image data stored in the storage 25 to a portable terminal 3 (external terminal), and also to an external system or a storage medium (external device).

According to the above, when the capturing is performed, the web page including the display image is displayed on the portable terminal 3. That is, the radiation image capturing apparatus 2 substitutes the console, and the capturing work flow is completed by using the radiation image capturing apparatus 2 and the typical portable terminal 3.

The portable terminal 3 uses the web browser to display the data of the web contents received from the radiation image capturing apparatus 2. Therefore, the explicit installing of the application on the portable terminal 3 is not necessary. As a result, even if there is trouble in the portable terminal 3 or the portable terminal 3 runs out of batteries, other typical portable terminals can be used instead. Further, maintenance such as update of application in the portable terminal 3 due to update of programs in the radiation image capturing apparatus 2 is not necessary.

Although embodiments of the present invention have been described and illustrated in detail, the disclosed embodiments are made for purposes of illustration and example only and not limitation. The scope of the present invention should be interpreted by terms of the appended claims.

The entire disclosure of Japanese Patent Application No. 2017-139604 filed on Jul. 19, 2017 is incorporated herein by reference in its entirety.

What is claimed is:

1. A cassette-type radiation image capturing apparatus which includes a radiation detector including a substrate in which a plurality of radiation detecting elements are arranged two dimensionally, the plurality of radiation detecting elements receiving radiation and generating charge in an amount according to an amount of the received radiation, the radiation image capturing apparatus comprising:
   a reader which reads the amount of charge generated in each of the plurality of radiation detecting elements as a signal value, and generates image data based on the signal value;
   a storage which stores the image data generated by the reader; and
   a hardware processor which obtains capturing order information from an external device, generates web contents which include the capturing order information in response to a request from a portable terminal which includes a web browser, and transmits data of the generated web contents to the portable terminal.

2. The cassette-type radiation image capturing apparatus according to claim 1, wherein:
   the hardware processor performs a predetermined image process on the image data and generates processed image data;
   the generated processed image data is stored in the storage;
   the capturing order information is linked to at least one of the image data and the processed image data to be stored in the storage; and
   the one of the image data and the processed image data which is linked to the capturing order information is transmitted to the portable terminal or the external device.

3. The cassette-type radiation image capturing apparatus according to claim 2, wherein the hardware processor obtains at least either one of past image data and past processed image data from the external device.

4. The cassette-type radiation image capturing apparatus according to claim 1, wherein the hardware processor includes in the data of the web contents a processing program which is executed on the web browser.

5. A radiation image capturing system comprising:
   a cassette-type radiation image capturing apparatus according to claim 1; and
   a portable terminal which includes a display and a web browser, and which is connected to communicate with the cassette-type radiation image capturing apparatus.

* * * * *